United States Patent [19]

Russo et al.

[11] Patent Number: 4,655,095

[45] Date of Patent: Apr. 7, 1987

[54] COMPOUND VALVE

[75] Inventors: Manuel A. Russo, Holliston; William Richards, Medway, both of Mass.

[73] Assignee: Millipore Corporation, Bedford, Mass.

[21] Appl. No.: 847,282

[22] Filed: Apr. 2, 1986

[51] Int. Cl.⁴ ............................................. G01N 1/00
[52] U.S. Cl. ............................. 73/864.83; 73/864.84; 251/314
[58] Field of Search ........... 73/864.81, 864.83, 864.84, 73/864.85, 864.86, 864.87, 864.21, 863.71, 863.72, 61.1 C, 23.1; 251/310, 314; 137/595, 625, 47

[56] References Cited

U.S. PATENT DOCUMENTS

| | | | |
|---|---|---|---|
| 1,060,791 | 5/1913 | Schaller | 251/310 |
| 1,469,421 | 10/1923 | Lenz | 251/310 |
| 2,467,065 | 4/1949 | White | 137/595 |
| 2,594,173 | 4/1952 | Jensen et al. | 251/310 |
| 3,021,713 | 2/1962 | Wright | 73/23.1 |
| 3,061,268 | 10/1962 | Zawacki | 251/314 |
| 3,195,856 | 7/1905 | Arrison | 251/314 |
| 3,237,644 | 3/1966 | Beck et al. | 251/314 |
| 3,687,416 | 8/1972 | Mueller | 251/314 |
| 3,916,692 | 11/1975 | Abrahams et al. | 73/864.84 |
| 4,094,196 | 6/1978 | Friswell | 73/864.21 |
| 4,533,113 | 8/1985 | Francart, Jr. | 137/595 |

Primary Examiner—Stewart J. Levy
Assistant Examiner—Robert R. Raevis
Attorney, Agent, or Firm—Hamilton, Brook, Smith & Reynolds

[57] ABSTRACT

The invention resides in a compound valve having utility in a sample injector for a liquid chromatograph. The valve has a pair of rotary spool valves (52, 54), each valve has a shaft (60) with an axial bore (64) in one end and a radial bore (66) communicating with the axial bore. A valve seal (70) surrounds the shaft. A pair of radial passageways (77, 78) in the seal are aligned diametrically and lie in a common plane with the radial bore (66) in the valve shaft. A pinion (62) is fixed to each shaft and a common driving gear (68) engages each pinion to rotate both shafts simultaneously through 180° to place the radial bores in the shafts in communication selectively with either radial passageway in the valve seals.

8 Claims, 7 Drawing Figures

COMPOUND VALVE

FIELD OF THE INVENTION

This invention relates to mechanism used to inject a liquid test sample into apparatus for analyzing a sample. It has particular utility as a sample injector for liquid chromatographs.

BACKGROUND OF THE INVENTION

A liquid chromatograph is an instrument for analyzing liquids into which a sample to be analyzed is introduced via a stream of solvent from an injector. The flowing stream of solvent, known as the mobile phase, forces the sample through a narrow bore transport tube to a column. The column is a larger diameter tube packed with a bed of small particles known as the stationary phase.

The sample mixture is separated as a result of differential partition between the stationary and mobile phases and as the mobile phase is forced through the stationary phase, a multiple component sample is separated into discrete zones or bands. The bands continue to migrate through the bed and eventually passes out of the column (a process known as elution) and through any one of number of detectors which provide input to a recording device, one example being a strip chart recorder. A deflection of the pen of the recorder indicates the elution of one or more chromatographic bands. Recorder tracing from the elution of a single band is called a peak and the collection of peaks which result from an injected sample comprise the chromatogram. Peaks are usually identified by their retention time or volume.

A phenomenon encountered in liquid chromatography is called "peak spreading" which results from the sample being excessively diluted in the injector apparatus before entering the column. Consequently, the peaks appearing on the analytical chart which are descriptive of the composition leaving the column, are less distinct, i.e., they are "spread" into lower less definable shapes.

It is one of the objectives of this invention to address the problem of "peak spreading".

Numerous prior art mechanisms have been developed with this objective in mind. One device is shown in U.S. Pat. No. 3,916,692 to Abrahams et al. A basic flow pattern is described in the Abrahams et al. patent; a parallel path conduit is employed, one path is a sample loop conduit and the second path is a primary conduit. The conduits are connected in parallel in the loading phase and a liquid sample to be tested is loaded into the sample loop until it is filled. At this time, the sample loop is not in communication with the primary conduit.

The primary conduit includes flow restricting means or bypass restrictor and when a solvent or mobile phase is pumped through the primary conduit, none of the mobile phase (also known as the carrier fluid) flows through the sample loop. The flow of the carrier fluid is blocked by closed valves during the time the sample loop is being filled. Upon the opening of the valves which heretofore blocked the flow of carrier fluid through the sample loop, the high pressure carrier fluid forces the sample from the loop into the column containing the stationary phase. Because of the presence of the bypass restrictor in the primary conduit, essentially most of the flow but not all of the carrier fluid is diverted to the sample loop to force the sample into the column. The Abrahams et al. patent disclosed a mechanism for accomplishing this.

Subsequently, U.S. Pat. No. 4,094,196 to Friswell disclosed a liquid sample injector employing a sliding spool valve. It employs a hollow needle with an opening at one end, movable longitudinally to a position where the opening is immersed in a liquid sample. The sample is drawn into the needle and then the needle is moved to a second position with the opening in the main solvent stream. Valves are actuated which divert the main solvent stream through the needle sweeping the sample out to the system for analysis. Sample injectors made in accordance with the Friswell patent have proven to be commercially successful being somewhat complex to manufacture.

It is, thus, another object of this invention to produce a liquid sample injector which is easy to manufacture and which will substantially reduce peak spreading by reducing to a minimum the dilution of the sample in the high pressure liquid phase stream.

SUMMARY OF THE INVENTION

The invention resides in a compound valve having utility in a sample injector for liquid chromatography which includes a pair of rotary spool valves. Each of the valves has a shaft including an axial bore on one end and a radial bore communicating with the axial bore. A pinion is fixed to each shaft and engages a common driving gear whereby both pinions and consequently the valve shafts are rotated simultaneously. A valve seal surrounds each shaft and is locked in position. Diametrically opposed passageways in each valve seal are aligned and lie in a common plane with the radial bore in the associated valve shafts. Rotation of the shafts simultaneously through 180° places the radial bores in communication selectively with either radial passageway in the valve seals. A seal retainer surrounds each valve shaft to load and maintain the radial passageways in the seal with the radial passageway in the shafts. Pressure means in engagement with the seal retainer maintains the passageways in the shaft and in the seals in alignment.

Both rotary spool valves are located in one valve body. There is a primary fluid conduit in permanent open communication with a primary fluid inlet passageway and a primary fluid exit passageway in the valve body. The rotary spool valve shafts are disposed between the primary conduit and the secondary conduit or sample loop conduit. The axial bore in the shafts are in permanent open communication with the secondary fluid or sample loop. The rotary spool valve shafts are rotated simultaneously from a first position, where flow is blocked by the valve shafts, to a second position wherein the primary and secondary fluid conduits are placed in communication through the valve shafts. At this time, communication between the secondary fluid inlet passageway and the secondary fluid exit passageway is blocked by the valve shaft. The driving gear may be rotated either manually or by appropriate motor means.

The above and other features of the invention including various novel details of construction in combinations of parts will now be more particularly described with reference to the accompanying drawings and pointed out in the claims. It will be understood that the particular compound valve for sample injector for liquid chromotagraphs embodying the invention is shown by way of illustration only and not as a limitation of the invention. The principles and features of this invention may be employed in varied and numerous embodiments without departing from the scope of the invention.

BEST MODE OF THE INVENTION

Figure 1:
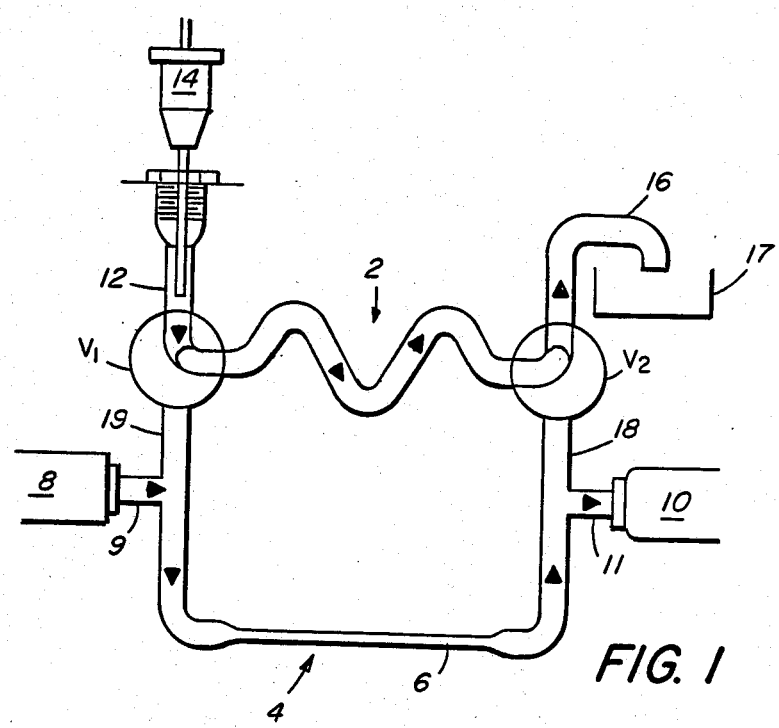
FIG. 1 is a schematic showing of the apparatus in the sample loading phase.
Figure 2:
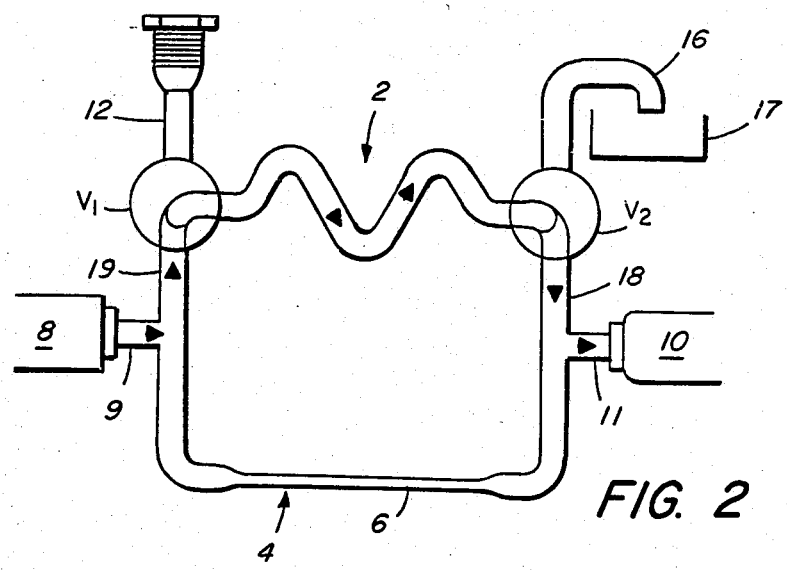
FIG. 2 is a schematic view similar to FIG. 1 showing the apparatus in the sample injecting phase.

Referring first to FIGS. 1 and 2 wherein the basic flow pattern of a liquid chromatograph is indicated schematically, FIG. 1 showing the sample loading phase and FIG. 2, the sample injecting phase. The conduit includes a sample loop conduit 2, and a primary conduit 4 having flow restrictor means 6 in the form of reduced diameter conduit. The parallel conduits 2 and 4 are joined at rotary spool valves $V_1$ and $V_2$. The mobile phase, fluid or solvent passes from a pump 8 to a column 10 which contains the bed of small particles known as the stationary phase.

In the loading phase, the sample to be analyzed enters the system through an inlet 12 which is in communication with the sample loop 2. The sample may be loaded, for example, by a syringe 14. The sample loop conduit communicates with a sample excess outlet passageway 16 to collecting means 17.

During the loading phase, the solvent flows under pressure from the pump 8 through the conduit 4 including the flow restrictor means 6 to the column 10. The passageways of both rotary spool valves, $V_1$ and $V_2$ are closed to conduit 4. The sample is loaded into the inlet 12, filling the sample loop 2 conduit, excess sample, flowing out of the conduit 16.

When the sample loop has been filled, the rotary spool valves, $V_1$ and $V_2$, are simultaneously indexed to the injecting phase (see FIG. 2). This indexing of valve $V_1$ places the primary conduit 4 and the pump 8 in communication with the sample loop 2 via a conduit 19. The corresponding indexing of valve $V_2$ places the sample loop 2 in communication with the column 10 by way of a conduit 18. At this time, the flow of solvent from the pump 8 forces the sample into the column 10, with a very small amount of solvent continuing to pass through the restrictor 6.

The rotary spool valves, $V_1$ and $V_2$, are essentially one valve since they are operated in synchronism and are embodied in one valve body as will be described with reference to FIGS. 3, 4, and 5. The valve body is generally indicated 20 and includes four component sections 22, 24, 26, and 28.

Figure 4:
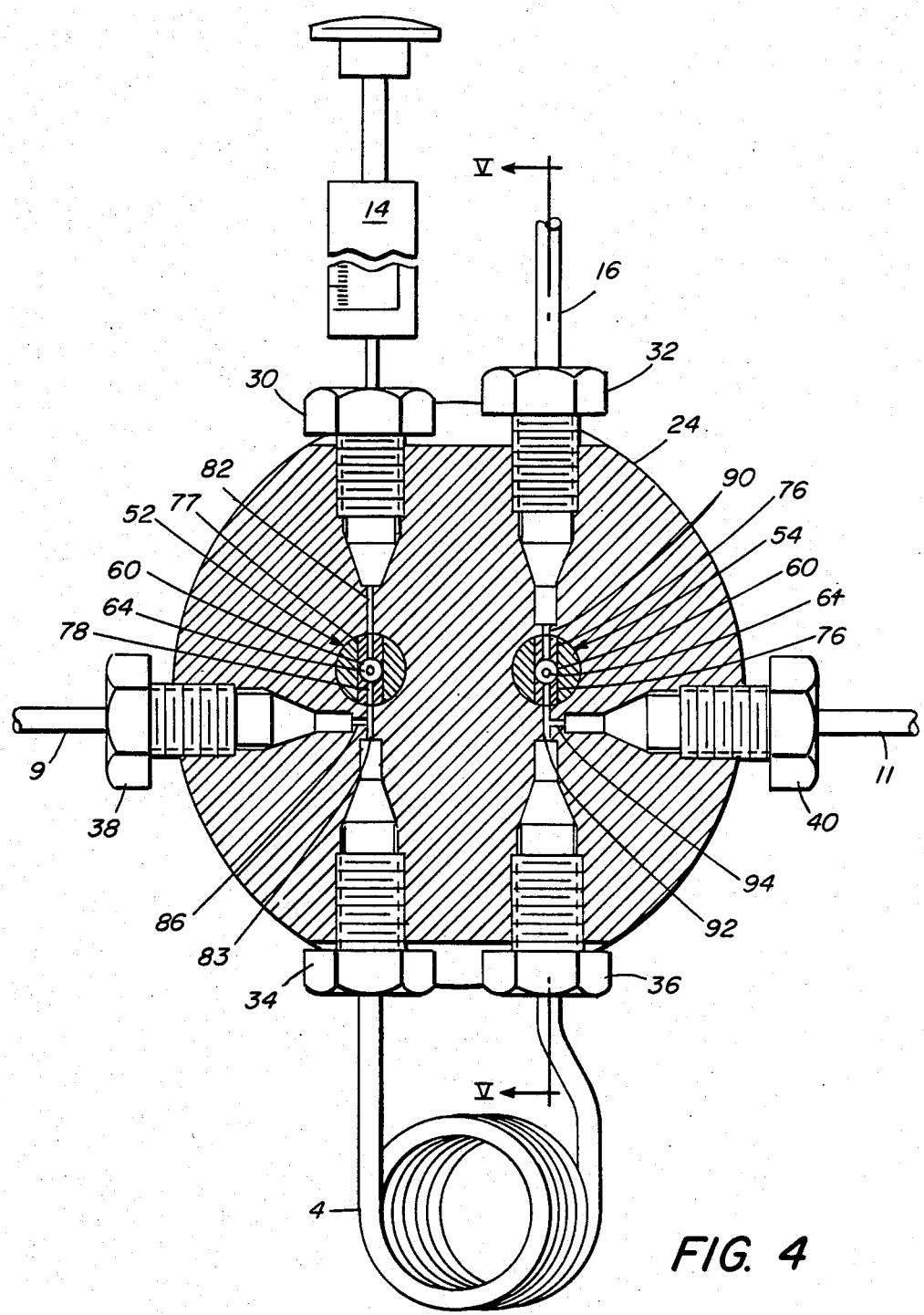
FIG. 4 is a section of the valve body taken on the line IV—IV on FIG. 3.

Referring to FIG. 4, a pair of fittings 30 and 32 are threaded into the valve body portion 24. They are coplanar with their axes in parallel alignment. Another pair of fittings 34 and 36 are also threaded into the valve body portion 24 and they, too, are coplanar and aligned with the fittings 30 and 32. The fittings 34 and 36 communicate with the bypass conduit 4 including the restrictor 6. The fitting 32 communicates with the sample excess conduit 16 and the fitting 30 communicates with the syringe 14 that loads the sample.

Also, coplanar with the fittings 30, 32, 34, and 36, are fittings 38 and 40, the fitting 38 communicating with a solvent inlet passageway 9 and the fitting 40 communicating with the passageway 11 which communicates with the column containing the stationary phase.

Figure 3:
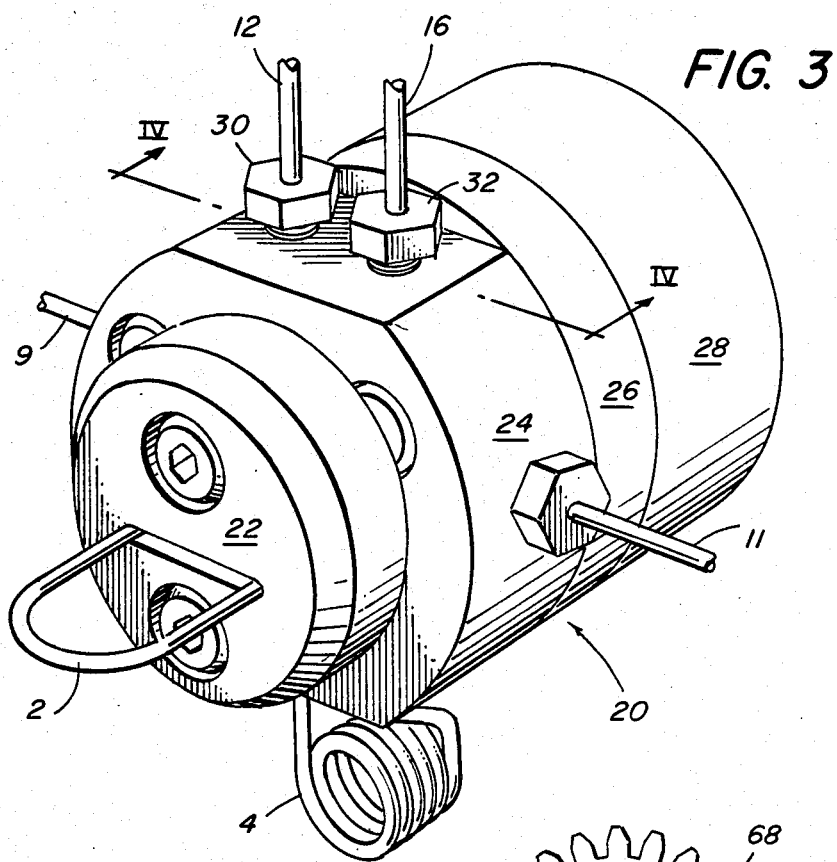
FIG. 3 is a perspective view of the valve body.

As seen in FIG. 3, a portion of the sample loop 2 is located outside of the valve body portion 22, and while it may assume any shape, it is a conduit formed in a U-shaped configuration. Inside the valve body portion 22, the sample loop 2 communicates with a pair of parallel rotary spool valves 52, 54 in the valve body. These rotary spool valves are disposed horizontally as shown in FIG. 5 and aligned vertically, as seen in FIG. 4, with the fittings 30, 32, 34, and 36.

Figure 7:
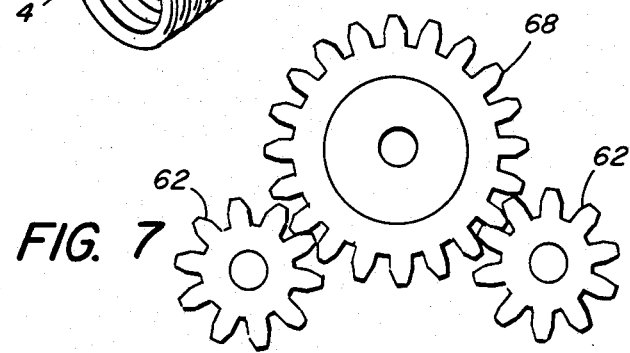
FIG. 7 is a sectional view of the rotary spool valve gear train taken on the line VII—VII of FIG. 5.
Figure 6:
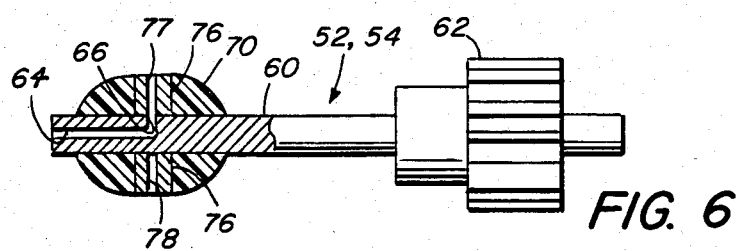
FIG. 6 is an enlarged view partially in section of one of the rotary spool valves.

As seen in FIG. 6, each of the rotary spool valves 52, 54 each include a shaft 60 which mounts a pinion gear 62 near one end and on the opposite end it has an axial bore 64. Intersecting the bore 64 is a radial bore 66. The pinion gear 62 of each valve meshes with a common driving gear 68, FIG. 7, located in the valve body portion 28. The gear 68 is attached to a drive shaft 71 which may be rotated either manually by an appropriate handle or automatically by a motor.

Figure 5:
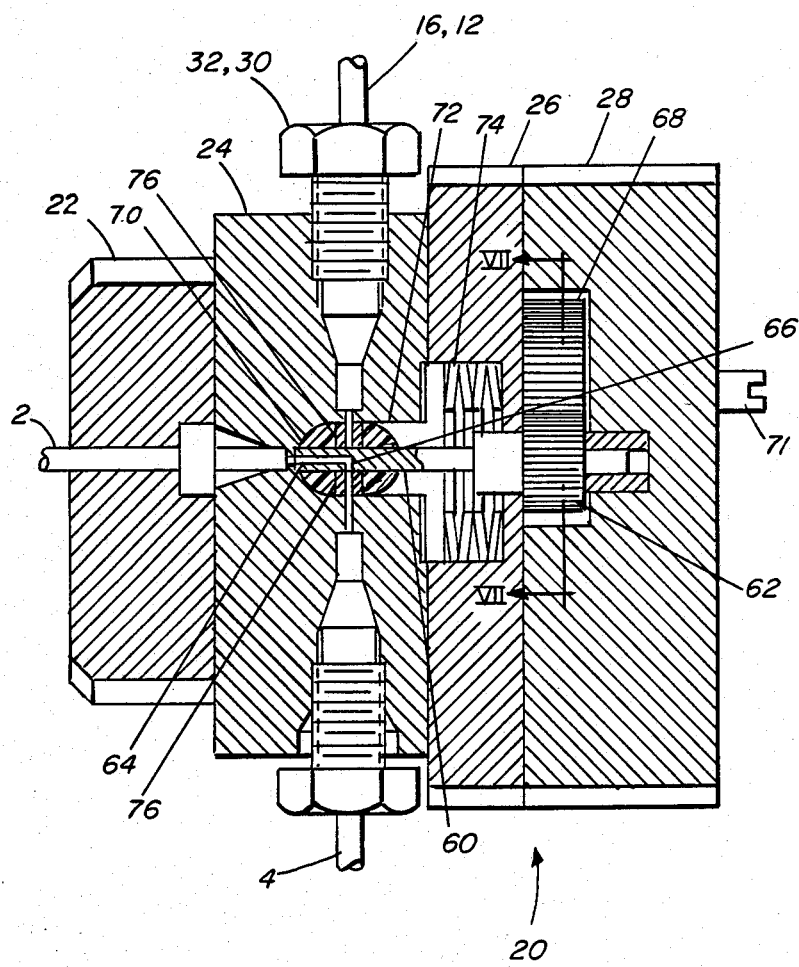
FIG. 5 is a section taken on the line V—V of FIG. 4.

Surrounding the shaft 60 of each of the rotary spool valves 52, 54 is a stationary seal 70 which is held within the valve body portion 24 by a seal retainer 72 which is urged to the left, as seen in FIG. 5, by a plurality of stacked Bellville washers 74 which bear against the seal retainer 72. The stationary seal includes a pair of vertically aligned seal inserts 76 having vertical bores 77 and 78, 180 degrees apart.

As seen in FIGS. 4 and 5, each valve seal 70 is designated as being made of plastic and is substantially ellipsoidal, being shown in FIG. 5 in cross-section as an ellipse and in FIG. 4 in cross-section as circular. The cavity in the valve body portion 24, in which the left hand portion (as viewed in FIG. 5) of the seal 70 fits, is semi-ellipsoidal. The surface of the seal retainer 72 which engages the right hand portion of the seal 70 is also semi-ellipsoidal. Since the Bellville washers urge the seal retainer 72, and hence the seal 70, toward the left as viewed in FIG. 5, the engaging ellipsoidal surfaces of the body portion 24 and the seal retainer 72 exert components of force in a direction radially of the shaft 60 to load and maintain the seal radially against the shaft. The horizontal component urges the seal 70 axially of the shaft 70 to maintain the axial passageway 66 in alignment with the passageways 77 and 78 in the seal, depending on the position of rotation of the shaft 60, as well as maintaining the passageways in the seal 70 in alignment with the passageways 82, 83, 90 and 92 in the valve body.

Referring to FIG. 4, the bore 77 in the valve 52 and the seal 70 communicates with vertical passageway 82 which is formed in the valve body portion 24 which in turn communicates with the sample inlet fitting 30. The bore 78 communicates with a passageway 83 which, in turn, communicates with the fitting 34 attached to the primary conduit 4.

Intersecting the passageway 83 is a horizontal passageway 86 which communicates with the fitting 38 which, in turn, communicates with the flow inlet passageway 9 which is connected to the solvent pump 8. In like manner, the rotary spool valve 54 communicates with a vertical passageway 90 which, through the fitting 32, communicates with the sample excess conduit 16. A vertical aligned passageway 92 communicates with the fitting 36 connected to the primary conduit 4. Through an intersecting passageway 94, the valve 54 communicates with the fitting 40 which, through the conduit 11, directs the sample to the column 10.

The axial passageways 64 in the valve shafts 60 communicate directly, and at all positions of rotation of the rotary spool valve, with the sample loop 2.

As seen in FIG. 4, the solvent inlet conduit 9 is always in communication with the primary conduit 4 and restrictor 6. The primary conduit 4 is always in communication with the conduit 11 that leads to the column 10, as a result of the intersecting passageways 86, 83 and 92, 94.

Turning the driving gear 68, which is meshed with the pinions 62, 62, causes the valve shafts 60 to rotate through 180°. From the position shown in FIG. 5 (which represents the injecting phase) where the radial passageway 66 is in the lower position, placing the primary conduit 4 in communication with the sample loop 2, (as shown schematically in FIG. 2), the valve shafts 60 are rotated 180°. In this latter position, the shaft 60 interrupts communication between the sample loop 2 and the primary conduit 4 while the radial passageways 66 in the shaft 60 simultaneously opens the sample loop 2 to the introduction of sample solution. Any excess sample is then free to pass out of the sample excess outlet conduit 16 via the rotary spool valve 54 which was also rotated 180°. This is known as the loading phase and shown schematically in FIG. 1.

We claim:

1. A compound valve comprising:
    a single valve body,
    a pair of rotary spool valves located in the valve body,
    each valve having a shaft,
    an axial bore in one end of each shaft and a radial bore communicating with the axial bore,
    a pinion fixed to each shaft and a common driving gear engaging both pinions to rotate both valve shafts simultaneously,
    a pair of valve seals, each seal surrounding one of the shafts,
    the valve seals being substantially ellipsoidal in configuration,
    a pair of semi-ellipsoidal cavities in the valve body, each cavity engaging substantially half of one valve seal, and
    a pair of seal retainers, each having a semi-ellipsoidal cavity engaging the other half of one valve seal.

2. A compound valve in accordance with claim 1 wherein there are pressure means in engagement with each seal retainer to load and maintain the seal radially against the shaft.

3. A compound valve comprising:
    a single valve body,
    a pair of rotary spool valves located in the single valve body,
    each valve having a shaft,
    an axial bore in one end of each shaft and a radial bore communicating with the axial bore,
    a pair of valve seals, each seal surrounding one of the shafts,
    the valve seals being substantially ellipsoidal in configuration,
    a pair of semi-ellipsoidal cavities in the valve body, each cavity engaging substantially half of one valve seal,
    a pair of seal retainers, each having a semi-ellipsoidal cavity engaging the other half of one valve seal,
    a pair of radial passageways in each seal aligned diametrically and lying in a common plane with the radial bore in the valve shaft that the seal surrounds, and
    a pinion fixed to each shaft and a common driving gear engaging both pinions to rotate both valve shafts simultaneously,
    whereby rotation of the shafts through 180°, places the radial bores in both shafts selectively in communication with either radial passageway in the valve seal that surround the shaft.

4. A compound valve in accordance with claim 3 wherein there are pressure means in engagement with each seal retainer to load and maintain the seal radially against the shaft.

5. A compound valve in accordance with claim 3 wherein there are pressure means in engagement with each seal retainer to maintain the passageways in the seal in alignment with the radial passageway in the shaft.

6. A compound valve for controlling the flow of a primary fluid and a secondary fluid comprising:
    a single valve body,
    a primary fluid conduit in permanent open communication with a primary fluid inlet passageway and a primary fluid exit passageway,
    a secondary fluid conduit,
    a pair of rotary spool valves in the valve body disposed between the primary fluid conduit and the secondary fluid conduit,
    each rotary spool valve having a shaft,
    an axial bore in each shaft in permanent open communication with the secondary fluid conduit and a radial bore in each shaft in communication with axial bore,
    a pair of valve seals, each seal surrounding one of the shafts,
    the valve seals being substantially ellipsoidal in configuration,
    a pair of semi-ellipsoidal cavities in the valve body, each cavity engaging substantially half of one valve seal,
    a pair of seal retainers, each having a semi-ellipsoidal cavity engaging the other half of one valve seal, and
    means for rotating both rotary spool valves simultaneously from a first position,
    wherein communication between the primary and secondary fluid conduits is blocked by the valve shafts, to a second position wherein the primary and secondary fluid conduits are placed in communication.

7. A compound valve according to claim 6 wherein the means for rotating the rotary spool valves comprises a pinion on each rotary spool valve in engagement with a common driving gear.

8. A compound valve in accordance with claim 6 wherein there are pressure means in engagement with each seal retainer to load and maintain the seal radially against the shaft.

* * * * *